US012748099B2

(12) United States Patent
Nguyenpham et al.

(10) Patent No.: US 12,748,099 B2
(45) Date of Patent: Sep. 29, 2026

(54) NANOPORE FORMATION METHOD

(71) Applicant: HITACHI HIGH-TECH CORPORATION, Tokyo (JP)

(72) Inventors: Hai Huy Nguyenpham, Tokyo (JP); Yoshimitsu Yanagawa, Tokyo (JP); Rena Akahori, Tokyo (JP)

(73) Assignee: HITACHI HIGH-TECH CORPORATION, Tokyo (JP)

(*) Notice: Subject to any disclaimer, the term of this patent is extended or adjusted under 35 U.S.C. 154(b) by 271 days.

(21) Appl. No.: 18/570,179

(22) PCT Filed: Jul. 1, 2021

(86) PCT No.: PCT/JP2021/025047
§ 371 (c)(1),
(2) Date: Dec. 14, 2023

(87) PCT Pub. No.: WO2023/276129
PCT Pub. Date: Jan. 5, 2023

(65) Prior Publication Data

US 2024/0385169 A1 Nov. 21, 2024

(51) Int. Cl.
*G01N 33/487* (2006.01)
*G01N 27/02* (2006.01)
(Continued)

(52) U.S. Cl.
CPC ..... *G01N 33/48721* (2013.01); *G01N 27/026* (2013.01); *G01N 27/3278* (2013.01); (Continued)

(58) Field of Classification Search
CPC ......... G01N 33/48721; G01N 33/5438; G01N 33/48728; G01N 27/026; G01N 27/3278; G01N 27/4167; G01N 27/00
See application file for complete search history.

(56) References Cited

U.S. PATENT DOCUMENTS

2016/0327513 A1* 11/2016 Yanagi ............ G01N 27/44791
2017/0268054 A1 9/2017 Akahori et al.
(Continued)

FOREIGN PATENT DOCUMENTS

JP 2019-74495 A 5/2019
WO 2015/097765 A1 7/2015
(Continued)

OTHER PUBLICATIONS

Kwok et al., Nanopore fabrication by controlled dielectric breakdown, Plos One, 2014, 9(3), e92880 (Year: 2014).*
(Continued)

*Primary Examiner* — Shizhi Qian
(74) *Attorney, Agent, or Firm* — MATTINGLY & MALUR, PC

(57) ABSTRACT

A nanopore with a high yield and an appropriate size is formed. Thus, the present disclosure proposes a nanopore formation method for forming a nanopore in a membrane, the method including: introducing an aqueous solution at a first pH into a first solution tank and a second solution tank insulated by the membrane; securing hydrophilicity of a surface of the membrane; replacing the aqueous solution at the first pH in the first solution tank and the second solution tank with an aqueous solution at a second pH lower than the first pH after the hydrophilicity of the surface of the membrane is secured; and immersing an electrode in each of the first solution tank and the second solution tank containing the aqueous solution at the second pH to cause dielectric breakdown and form a nanopore in the membrane (see FIG. 4).

17 Claims, 9 Drawing Sheets

(51) Int. Cl.

*G01N 27/327* (2006.01)
*G01N 27/416* (2006.01)
*G01N 33/543* (2006.01)

(52) U.S. Cl.

CPC ... *G01N 27/4167* (2013.01); *G01N 33/48728* (2013.01); *G01N 33/5438* (2013.01)

(56) References Cited

U.S. PATENT DOCUMENTS

2019/0120792 A1* 4/2019 Yokoi .............. G01N 27/44791
2022/0381762 A1* 12/2022 Tezuka ............. G01N 33/48721
2022/0410149 A1* 12/2022 Deng ................ B01L 3/502715

FOREIGN PATENT DOCUMENTS

WO 2019/008736 A1 1/2019
WO 2020/194303 A1 10/2020
WO 2020/217330 A1 10/2020

OTHER PUBLICATIONS

Spiegelman et al., Increased hydrophilicity of silicon surface through plasma treatment with hydrogen peroxide gas, 2021 ECS Meet. Abstr., 2021 (Year: 2021).*
Chen et al., water adsorption on hydrophilic and hydrophobic surfaces of silicon, Journal of physical chemistry C, 2018, 122, 11385-11391 (Year: 2018).*
Yanagi et al., Stable fabrication of a large nanopore by controlled dielectric breakdown in a high-pH solution for the detection of various-sized molecules, Scientific Reports, 2019, 9, 13143 (Year: 2019).*
Zhang et al., Fabrication of nanopores using controlled dielectric breakdown, 2019 IEEE Int. Conf. on manipulation, manufacturing and measurement on nanoscale, Aug. 4-8, 2019 (Year: 2019).*
Arcadia et al., In situ nanopore fabrication and single-molecule sensing with microscale liquid contacts, ACS Nano,2017, 11, 4907-4915 (Year: 2017).*
Yanagi et al., Fabricating nanopores with diameters of sub-1 nm to 3 nm using multilevel pulse-voltage injection, Scientific Reports, 2014, 4, 5000; hereinafter Yanagi_I (Year: 2014).*
Leung et al., Mechanisms of solid-state nanopore enlargement under electrical stress, Nanotechnology, 2020, 31, 44LT01 (Year: 2020).*
Harold Kwok, et al., "Nanopore Fabrication by Controlled Dielectric Breakdown", PLoS ONE 9(3): e92880, 2014, DOI: https://doi.org/10.1371/journal.pone.0092880.
Itaru Yanagi, et al., "Stable fabrication of a large nanopore by controlled dielectric breakdown in a high-pH solution for the detection of various-sized molecules", Scientific Reports 9:13143, 2019, DOI: https://doi.org/10.1038/s41598-019-49622-y.
International Search Report of PCT/JP2021/025047 dated Sep. 21, 2021.
Chinese Office Action received in corresponding Chinese Application No. 202180098457.9 dated Apr. 30, 2026.
Saharia, J. et al., "Assessment of 1/f noise associated with nanopores fabricated through chemically tuned controlled dielectric breakdown", Electrophoresis Journal, 2021, pp. 899-909.

* cited by examiner

NANOPORE FORMATION METHOD

TECHNICAL FIELD

The present disclosure relates to a nanopore formation technique for forming a nanopore in a membrane.

BACKGROUND ART

Nanopore sensors have been developed as biological sample analyzers for analyzing molecules, particles, DNA, proteins, and the like, for example. The nanopore sensors each include a thin film (membrane) on which pores having a size larger than or equal to a size of a biological sample (sample), such as pores having a diameter of 1 nm to 100 nm, are formed. An aqueous solution is introduced into a first solution tank and a second solution tank insulated by the membrane. The biological sample (sample) is introduced into any one of the first solution tank or the second solution tank. Voltage is applied to measure an ion current flowing between electrodes immersed in the respective solution tanks. Object characteristics and structural characteristics of the biological sample can be detected by measuring a blocked ion current flowing when the biological sample passes through the pores.

The nanopore sensors are classified into two types including one type based on a biological membrane and the other type based on a solid-state membrane. The nanopore sensor using the biological membrane includes pores formed by floating proteins having pores of a nanometer size on a lipid bilayer membrane. In contrast, the nanopore sensor using the solid-state nanopore includes a membrane made of a high dynamic strength material such as silicon nitride (SiN), and pores of a nanometer size that are manufactured by electron beam irradiation to the membrane, a chemical etching technique, or a dielectric breakdown technique in which a voltage is applied to the membrane to form pores. The dielectric breakdown technique causes a potential difference in the membrane using an external power supply or the like to apply stress to the membrane, thereby forming a nanopore by dielectric breakdown. The dielectric breakdown technique has advantages such as an inexpensive nanopore manufacturing cost, user friendliness, on-site processing (processing at a user's place of use), and ability to form fresh nanopores because nanopores can be formed on a membrane immediately before a target sample is measured.

For example, PTL 1 or NPL 1 discloses formation of nanopores on a SiN membrane using a neutral pH aqueous solution (pH 7-7.5). The introduced aqueous solution may sometimes not come into contact with a surface of a dry membrane because the surface of the dry membrane becomes hydrophobic. Thus, a yield of nanopore formation may be deteriorated. The reason why a solid-state membrane becomes hydrophobic due to surrounding environment is considered to be that its surface is oxidized or/and unnecessary organic substances adhere to the surface. Thus, a laboratory is required to usually perform a treatment for hydrophilizing the membrane before use. In general, a laboratory performs hydrophilicity processing by piranha processing or plasma processing. However, when the nanopore sensor is commercialized, causing an end user to perform these dangerous processes is not realistic, and thus another alternative technique is required.

For example, PTL 2 discloses introduction of a method for storing a membrane in an aqueous solution at specific conditions such as the amount of water, temperature, and salinity. PTL 3 discloses introduction of a method for storing a membrane by attaching a hydrophilic surface and a protective layer containing a soluble substance to the membrane. PTL 4 discloses introduction of an electrowetting on dielectric (EWOD) method in which droplets of an aqueous solution are moved to a position of a membrane by applying high voltage to control hydrophobicity and a hydrophilic property, and this method also requires plasma treatment of a surface of the membrane. PTL 5 discloses introduction of a nanopore production method based on a pulsed laser in which piranha treatment is performed on a sample before measurement to achieve hydrophilicity.

CITATION LISTS

Patent Literatures

PTL 1: WO 2015/097765 A
PTL 2: WO 2019/008736 A
PTL 3: JP 2019-74495 A
PTL 4: WO 2020/217330 A
PTL 5: WO 2020/194303 A

Non Patent Literatures

NPL 1: Harold Kwok, Kyle Briggs, and Vicent Tabard-Cossa, "Nanopore fabrication by controlled dielectric breakdown", PLos ONE 9 (3), e 92880 (2014), DOI: https://doi.org/10.1371/journal.pone.0092880
NPL 2: Itaru Yanagi, Rena Akahori, and Ken-ichi Takeda, "Stable fabrication of a large nanopore by controlled dielectric breakdown in a high-pH solution for the detection of various-sized molecules", Scientific Reports 9, 13143 (2019), DOI: https://doi.org/10.1038/s41598-019-49622-y

SUMMARY OF INVENTION

Technical Problem

PTL 1 and NPL 1, however, cause a low yield of nanopore formation due to a dry membrane surface having hydrophobic characteristics although the dielectric breakdown is performed using a neutral pH aqueous solution without the piranha treatment or the plasma treatment. Additionally, requiring the piranha treatment or the plasma treatment to be performed at a user's place of use (on-site) causes problems that a user is burdened with performing processing and is unfavorable to safety, and thus is not realistic. Even when the alternative preservation techniques according to PTLS 2 and 3 are used, a preservation process itself may cause a burden on the user.

By contrast, an alkaline aqueous solution or a high pH aqueous solution has low surface tension characteristics, and so can wash away unnecessary substances that enter a position of a membrane and adhere to a surface of the membrane. NPL 2 describes nanopores that are formed on a membrane of about 20 nm using a high pH aqueous solution as described above. However, the high pH aqueous solution is used for a chemical etching process, so that a sub-nanometers to nanometers size of the nanopores to be formed cannot be controlled, and thus the membrane may be deteriorated. Precise control of nanopore size on the order of sub-nanometers is considered to be important in performing practical biological analysis such as DNA sequencing.

In view of such a situation, the present disclosure proposes a technique for forming a nanopore having a high yield and an appropriate size.

Solution to Problem

To solve the above problems, the present disclosure proposes a nanopore formation method for forming a nanopore in a membrane, the method including: introducing an aqueous solution at a first pH into a first solution tank and a second solution tank insulated by the membrane; securing hydrophilicity of a surface of the membrane; replacing the aqueous solution at the first pH in the first solution tank and the second solution tank with an aqueous solution at a second pH lower than the first pH after the hydrophilicity of the surface of the membrane is secured; and immersing an electrode in each of the first solution tank and the second solution tank containing the aqueous solution at the second pH to cause dielectric breakdown and form a nanopore in the membrane.

Further features related to the present disclosure will become apparent from the description herein and the accompanying drawings. Aspects of the present disclosure are achieved and implemented by elements, combinations of various elements, and aspects of the following detailed description and the scope of claims appended.

Advantageous Effects of Invention

According to the technique of the present disclosure, it becomes possible to form a nanopore having a high yield and an appropriate size.

DESCRIPTION OF EMBODIMENTS

Figure 1:
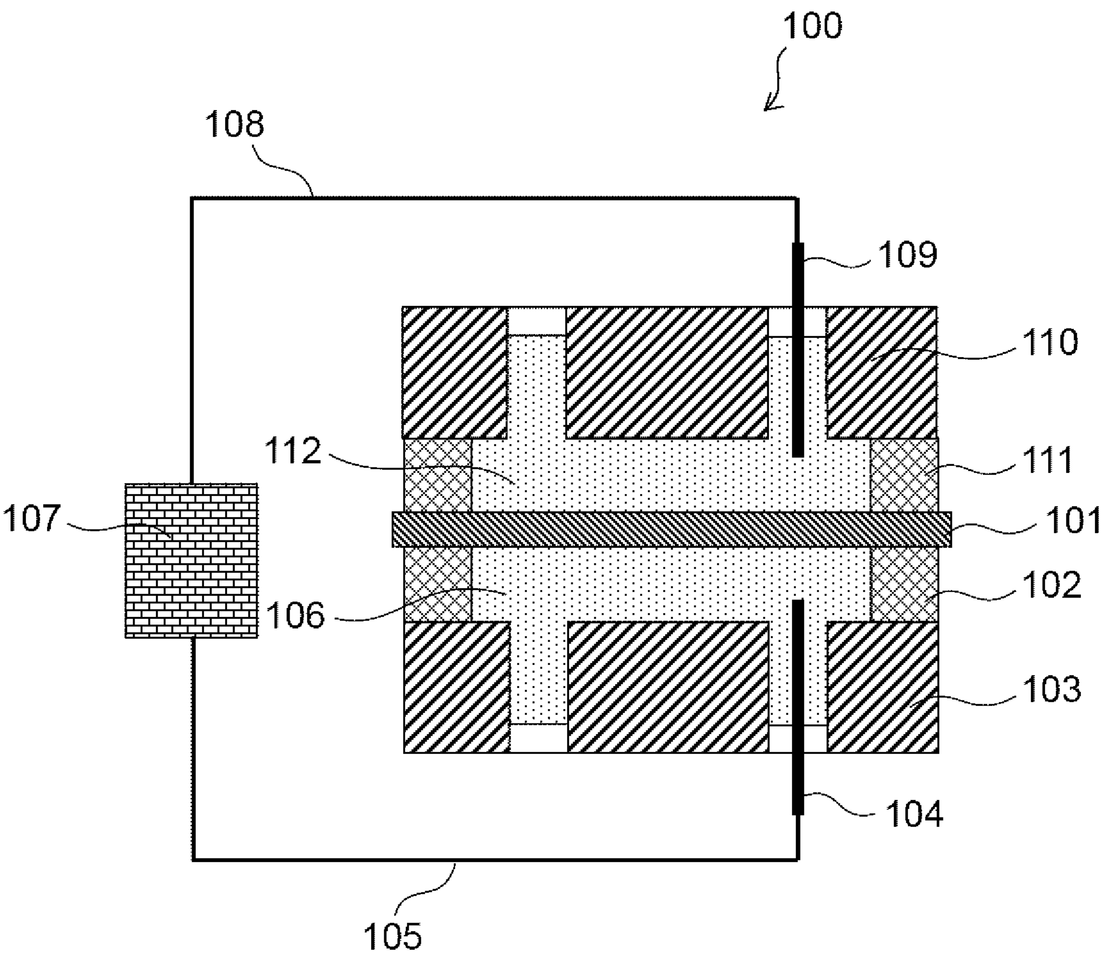
FIG. 1 is a diagram illustrating a configuration example of a nanopore sensing system before a nanopore is formed on a membrane.

A membrane in the present embodiment is not restricted in material, thickness, size, and number. There are no restrictions in composition on a high pH aqueous solution, a neutral pH aqueous solution used for nanopore formation, and an aqueous solution used for sample measurement, respectively in the present embodiment. A dielectric breakdown technique used for nanopore formation is merely an example. Various forms of dielectric breakdown technique can be applied. Although a capacitance noise measurement method is used when measuring RMS noise in the present embodiment, the present invention is not limited thereto.

<Overview>

(i) A nanopore sensing system in the present embodiment includes a dry membrane that is attached to a flow cell (a part of the nanopore sensing system) before a nanopore is formed to insulate a first solution tank and a second solution tank of the flow cell. A high pH aqueous solution (first pH aqueous solution) is introduced (filled) into each solution tank. An electrode is immersed in the solution in each bath and connected to an electric device unit capable of supplying a voltage or current. Before a nanopore is formed, capacitance noise is first measured in an unloaded state and a loaded state (a capacitance noise measurement process). It is checked whether a membrane surface becomes hydrophilic, and an aqueous solution is in contact with the membrane surface. When hydrophilicity of the membrane surface has been checked, the high pH aqueous solution in each solution tank is rapidly replaced by an aqueous solution at a lower pH (second pH aqueous solution: neutral pH aqueous solution) (aqueous solution replacement process). This is because the membrane is likely to be decomposed by a chemical etching process using a high pH aqueous solution. Subsequently, the electrode is immersed in each solution tank, and a voltage or a current is supplied by the electric device unit. As a result, dielectric breakdown occurs, and a nanopore is formed in the membrane.

(ii) In the capacitance noise measurement process, a DC voltage is applied between the two electrodes. Then, root mean square (RMS) noise or a noise of the electric device unit is monitored in a state without a load (a state where the electrode is not inserted into each of the solution tanks insulated by the membrane) and a state with a load (a state where the electrode is inserted into each of the solution tanks insulated by the membrane). Here, the DC voltage can be made lower than dielectric breakdown induction voltage of the membrane. For example, when a membrane having a thickness of 5 nm is used, the membrane has a dielectric breakdown voltage of 5 V, and thus capacitance noise is checked by applying a DC voltage from −2.5 V to 2.5 V. As described above, when a voltage lower than the dielectric breakdown induction voltage is applied in the capacitance noise measurement process, unnecessary dielectric breakdown can be prevented from occurring during the process.

In the present embodiment, when the capacitance noise with a load (RMS noise with a load) is several times (at least twice or more) higher than the capacitance noise without a load (RMS noise without a load), it is determined that the membrane surface becomes hydrophilic or the aqueous solution is in contact with the membrane surface. In contrast, when the RMS noise with a load is equal to or less than the RMS noise without a load, the aqueous solution may not be in contact with the membrane surface. Thus, the high pH aqueous solution (first pH aqueous solution) is taken out from each solution tank and reintroduced (filled). When the first pH aqueous solution is reintroduced, pH of the first pH aqueous solution may be further increased. The contact between the first pH aqueous solution and the membrane surface may be ensured by moving the first pH aqueous solution back and forth on the membrane surface (e.g., pipetting processing).

(iii) The aqueous solution replacement process is performed to take out the first pH aqueous solution (high pH aqueous solution) from each solution tank and to introduce a second pH aqueous solution (e.g., a neutral pH aqueous solution) at a pH lower than the first pH into each solution tank. This process may be performed several times to cause the aqueous solution in each bath to be reliably neutral. When the aqueous solution replacement process is performed, it may be checked whether the pH of the aqueous solution in each solution tank is neutral, for example.

(iv) A nanopore of a desired size can be formed on the membrane by causing dielectric breakdown. A sample can be introduced into any one of two solution tanks. When a voltage is applied between the electrodes of the respective solution tanks or when a current flows between the electrodes, an ion current is measured. A target molecule or particle can be detected by measuring the ion current (blockage current) when the target molecule or particle passes through a nanopore.

(v) A low utilization rate of a solid-state nanopore sensor due to hydrophobic properties of the dry membrane is overcome by introducing a high pH aqueous solution, as described above. After checking by measuring the capacitance noise that the aqueous solution is in contact with the membrane surface, the size of the nanopore is effectively controlled by rapidly replacing the aqueous solution with a neutral pH aqueous solution for nanopore production by the dielectric breakdown technique. Additionally, a burden of using advanced preservation processing of the membrane is also avoided.

<Configuration Example of Nanopore Sensing System>

FIG. 1 is a diagram illustrating a configuration example of a nanopore sensing system before a nanopore is formed on a membrane. A nanopore sensing system 100 includes a first solution tank 103 that contains an aqueous solution (e.g., 1M KCl pH 12.7), a second solution tank 110 that contains the aqueous solution (e.g., 1M KCl pH 12.7), liquid sealing gaskets 102 and 111, electrodes (e.g., an Ag/AgCl electrode) 104 and 109 immersed in the aqueous solution, an electric device unit 107 for supplying a power source and a current, an electric conducting wire 105 that connects the electrode 104 and the electric device unit 107, and an electric conducting wire 108 that connects the electrode 109 and the electric device unit 107. The membrane 101 is disposed in the nanopore sensing system 100 by being sandwiched by the liquid sealing gaskets 102 and 111. After the membrane 101 is disposed, aqueous solutions 106 and 112 are injected into the first solution tank 103 and the second solution tank 110, respectively. As the membrane 101, a dry SiN membrane or a multicomponent membrane can be used, for example.

<Checking Hydrophilicity of Membrane Surface and Forming Nanopore: Overview>

Figure 2:
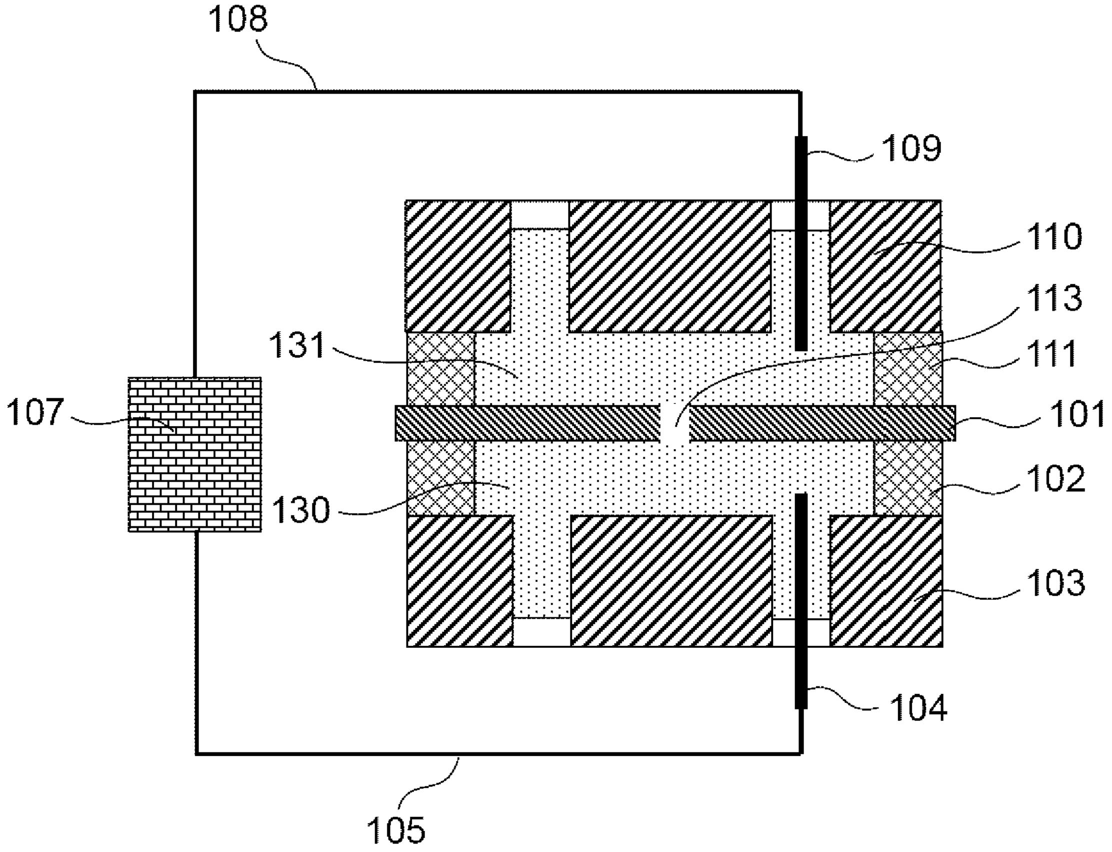
FIG. 2 is a diagram for illustrating an outline of processing from checking hydrophilicity of a membrane surface to forming a nanopore.

FIG. 2 is a diagram for illustrating an outline of treatment from checking hydrophilicity of a membrane surface to forming a nanopore.

First, capacitance noise (RMS noise) is measured while the 1M KCl pH 12.7 aqueous solutions 106 and 112 are contained in the first solution tank 103 and the second solution tank 110, respectively, as illustrated in FIG. 1, and it is checked whether the aqueous solutions 106 and 112 are in contact with respective surfaces of the membrane 101 (whether the surfaces of the membrane 101 has become hydrophilic) (details will be described later). After that, the 1M KCl pH 12.7 aqueous solutions 106 and 112 are discharged from the first solution tank 103 and the second solution tank 110, respectively, and the first solution tank 103 and the second solution tank 110 are filled with 1M KCl pH 7.5 aqueous solutions 130 and 131, respectively. That is, the 1M KCl pH 12.7 aqueous solutions 106 and 112 are replaced with the 1M KCl pH 7.5 aqueous solutions 130 and 131, respectively.

After the aqueous solutions are replaced, the electric device unit 107 applies a voltage or current based on the dielectric breakdown technique to enable a nanopore 113 of a desired size to be formed in the membrane 101 (pore size is controllable).

<Measurement of Sample>

Figure 3:
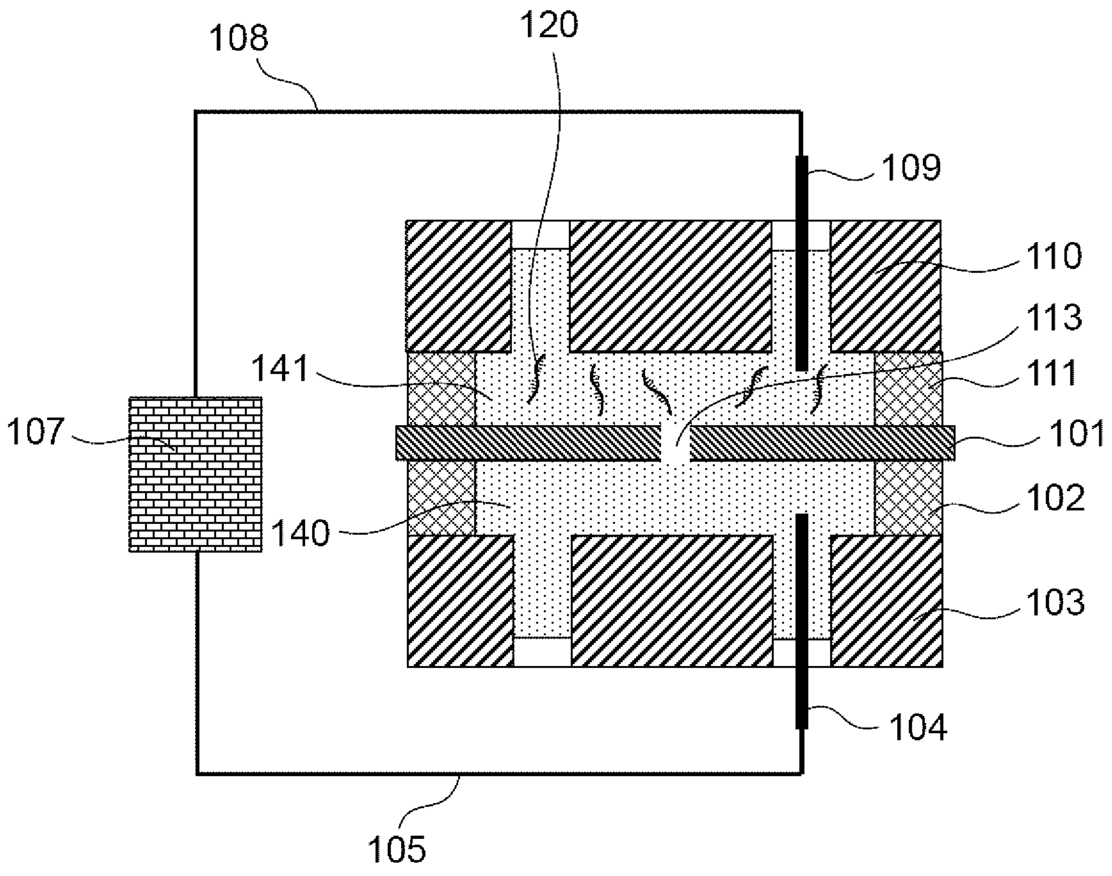
FIG. 3 is a diagram for illustrating an outline of processing of sample measurement in a nanopore sensing system 100.

FIG. 3 is a diagram for illustrating an outline of processing of sample measurement in the nanopore sensing system 100. As illustrated in FIG. 3, a sample 120 is introduced into any one of the first solution tank 103 and the second solution tank 110. Then, the electric device unit 107 applies a low voltage equal to or less than 20 V, such as 2 V or less, between the electrodes 104 and 109 to measure an ion current (blockage current) when the sample 120 passes through the nanopore 113. Aqueous solutions 140 and 141 are filled in the first solution tank 103 and the second solution tank 110, respectively, to measure a sample, and are each dedicated to a type of the sample (target sample) to be measured.

<Details of Processing from Forming Nanopore to Measuring Sample>

Figure 4:
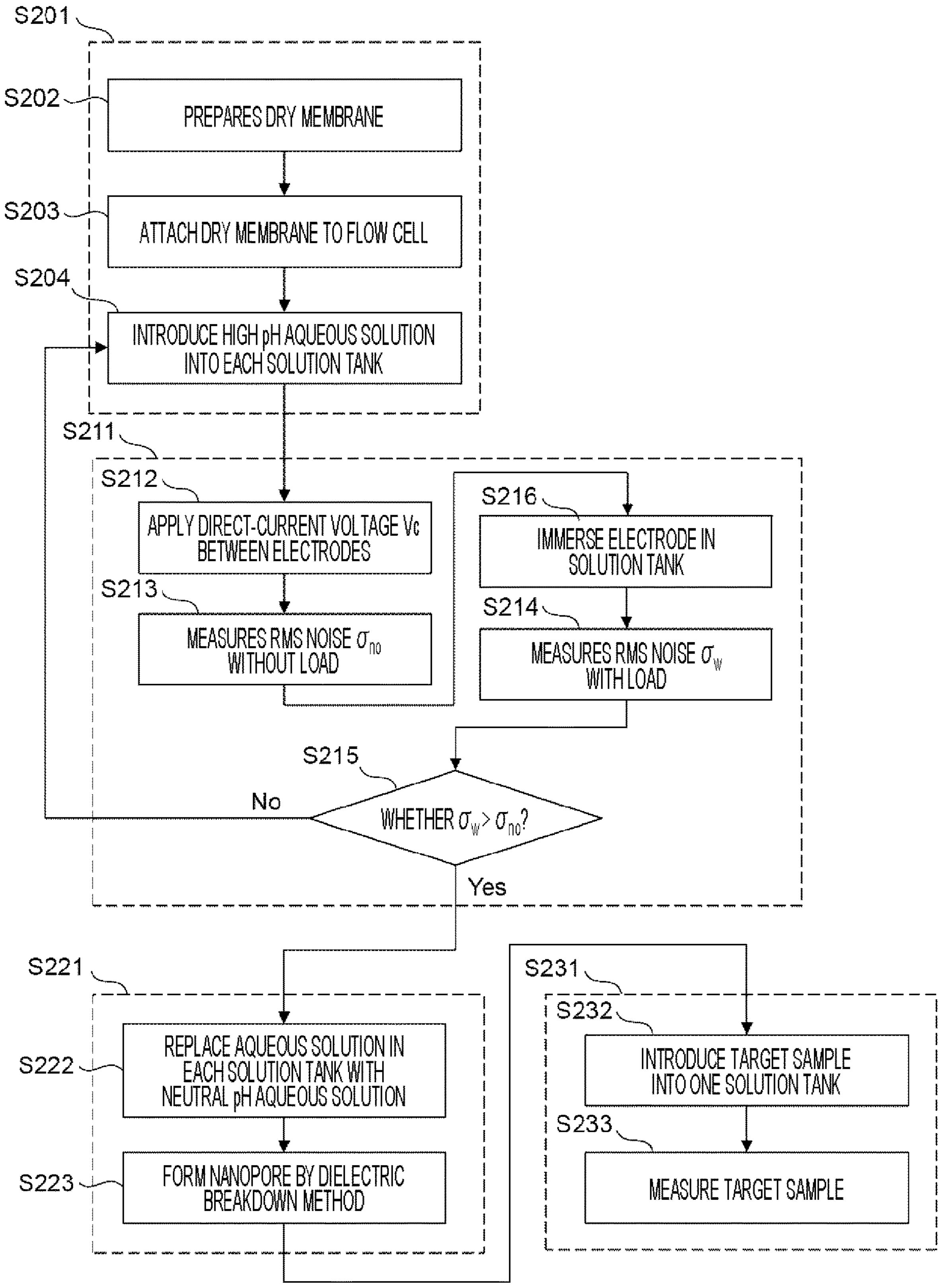
FIG. 4 is a flowchart for illustrating a flow of processing from forming a nanopore in a membrane to measuring a sample according to the present embodiment.

FIG. 4 is a flowchart for illustrating a flow of processing from forming a nanopore in a membrane to measuring a sample according to the present embodiment. The processing from forming a nanopore to measuring a sample according to the present embodiment includes hydrophilicity processing S201, hydrophilicity checking processing S211, nanopore forming processing S221, and sample measuring processing S231. That is, the processing according to the present embodiment enables measuring a sample using a nanopore with high yield and size controllable by immersing the membrane 101 in an aqueous solution at a high pH (aqueous solution at a first pH) to ensure hydrophilicity of the surfaces of the membrane 101 (step 201), checking whether the surfaces of the membrane 101 are actually hydrophilic (step 211), forming the nanopore by a dielectric breakdown method with an aqueous solution at a low pH (aqueous solution at a second pH lower than the first pH) (step 221), and measuring the sample (step 231).

(i) Step 201

(i-1) Step 202

First, an operator prepares a dry membrane 101.

(i-2) Step 203

Next, the operator attaches the dry membrane 101 to a flow cell. Here, the flow cell corresponds to a component part including the first solution tank 103, the second solution tank 110, and the liquid sealing gaskets 102 and 111 in the nanopore sensing system 100 (see FIGS. 1 to 3).

(i-3) Step 204

The operator introduces (fills) an aqueous solution at a high pH (higher than pH 8), or an aqueous solution at a first pH, such as an aqueous solution at a pH of 1M KCl of 12.7, into the first solution tank 103 and the second solution tank 110 of the flow cell.

(ii) Step 211

The hydrophilicity checking processing (step 211) includes the steps of: applying a DC voltage Vc between electrodes (step 212); measuring RMS noise without inserting an electrode into the flow cell (the first solution tank 103 and the second solution tank 110) (RMS noise measurement without a load: step 213); inserting an electrode into the flow cell (step 216); and measuring RMS noise (RMS noise measurement with a load: step 214).

(ii-1) Step 212

The operator applies the DC voltage (Vc) between the Ag/AgCl electrodes 104 and 109 using the electric device unit 107. At this stage, the Ag/AgCl electrodes 104 and 109 are not immersed in the aqueous solutions of the first solution tank 103 and the second solution tank 110, respectively. At this time, a low voltage of 10 V or less is applied, for example. This is to prevent undesired dielectric breakdown from occurring in step 214.

(ii-2) Step 213

The operator measures root mean square (RMS) noise (RMS noise $\sigma_{no}$ without a load) of the current in a state where the Ag/AgCl electrodes 104 and 109 are not immersed in the aqueous solution (aqueous solution at the first pH).

(ii-3) Step 216

The operator immerses the Ag/AgCl electrodes 104 and 109 in the aqueous solution (aqueous solution at the first pH).

(ii-4) Step 214

Subsequently, the operator measures root mean square (RMS) noise (RMS noise $\sigma_w$ with a load) of a current in a state where the Ag/AgCl electrodes 104 and 109 are immersed in an aqueous solution (aqueous solution at a first pH), that is in a state where the electrodes 104 and 109 are inserted into the first solution tank 103 and the second solution tank 110, respectively.

(ii-5) Step 215

The operator compares the RMS noise $\sigma_{no}$ without a load and the RMS noise $\sigma_w$ with a load. Specifically, it is determined whether the RMS noise $\sigma_w$ is several times (e.g., twice) larger than the RMS noise $\sigma_{no}$ without a load. When the RMS noise $\sigma_w$ with a load is larger than the RMS noise $\sigma_{no}$ without a load (Yes in step 215), it is confirmed that the surface of the membrane 101 has hydrophilicity (a hydrophilic property: a state in which the surface of the membrane 101 is completely in contact with the aqueous solution), and that the hydrophilicity checking processing (step 211) ends. Then, the processing proceeds to the nanopore forming processing S221. When the RMS noise $\sigma_w$ with a load is equal to or less than the RMS noise $\sigma_{no}$ without a load (No in step 215), the hydrophilicity of the surface of the membrane 101 is not ensured, and then the processing returns to step 204. In this case, the aqueous solutions (aqueous solution at the first pH, such as an aqueous solution of 1M KCl pH 12.7) in the first solution tank 103 and the second solution tank 110 are discharged in step 204, and the first solution tank 103 and the second solution tank 110 are filled with a new aqueous solution at the first pH. Then, the hydrophilicity checking processing (step 211) is performed again. When even the hydrophilicity checking processing performed multiple times (e.g., five times) fails to check hydrophilicity of the surface of the membrane 101 during the hydrophilicity checking processing performed again, the pH of the aqueous solution may be increased and set lower than 14.

Although the operator compares the RMS noise $\sigma_{no}$ without a load and the RMS noise $\sigma_w$ with a load in the above description, a computer (not illustrated) may be connected to the nanopore sensing system 100 to allow the computer to perform processing of the comparison. At this time, when the RMS noise $\sigma_w$ with a load is larger than the RMS noise $\sigma_{no}$ without a load, the computer controls a display device to display an instruction for transition of the processing to step 221 on a screen (not illustrated) of the display device, thereby enabling prompting the operator to perform the next nanopore forming processing. Then, when the RMS noise $\sigma_w$ with a load is equal to or less than the RMS noise $\sigma_{no}$ without a load, the computer contorols a display device to display an instruction for transition of the processing to step 204 on the screen (not illustrated) of the display device, thereby enabling prompting the operator to perform the hydrophilicity checking processing again. Alternatively, the RMS noise $\sigma_{no}$ without a load may be measured in advance and stored in a memory (not illustrated) to read out the RMS noise $\sigma_{no}$ without a load from the memory when the hydrophilicity checking processing is performed, thereby comparing the RMS noise $\sigma_{no}$ with the RMS noise $\sigma_w$ with a load.

(iii) Step 221

(iii-1) Step 222

The operator discharges the aqueous solution at the first pH with which the first solution tank 103 and the second solution tank 110 are filled. Instead, the operator fills an aqueous solution at the second pH lower than the first pH, such as a neutral aqueous solution, more particularly an aqueous solution of 1M KCl pH 7.5 (replacement of the aqueous solution).

(iii-2) Step 223

The operator operates the electric device unit 107 to apply a voltage between the electrodes 104 and 109 or allows a current to flow therebetween to cause dielectric breakdown, and forms the nanopore 113 having a desired size in the membrane 101 as illustrated in FIG. 2.

(iv) Step 231

As in the nanopore forming processing (step 221), the first solution tank 103 and the second solution tank 110 in the sample measuring processing are filled with the aqueous solution at the second pH, such as a neutral aqueous solution, more specifically an aqueous solution of 1M KCl pH 7.5, in which a type of the aqueous solution (such as KCl) rather than pH varies depending on a type of sample to be measured and introduced.

(iv-1) Step 232

As illustrated in FIG. 3, the operator introduces the sample (target sample) 120 to be measured into any one of the first solution tank 103 and the second solution tank 110.

(iv-2) Step 233

The operator operates the electric device unit 107 to apply a low voltage, such as a voltage lower than 20 V, and more specifically lower than 2 V, between the electrodes 104 and 109 to measure an ion current (blockage current) when the sample 120 passes through the nanopore.

<Detailed Content of Nanopore Forming Processing in Step 223>

FIGS. 5 to 8 are each a flowchart illustrating detailed contents (example) of nanopore forming processing using the dielectric breakdown technique. Here, four modes will be described.

Figure 5:
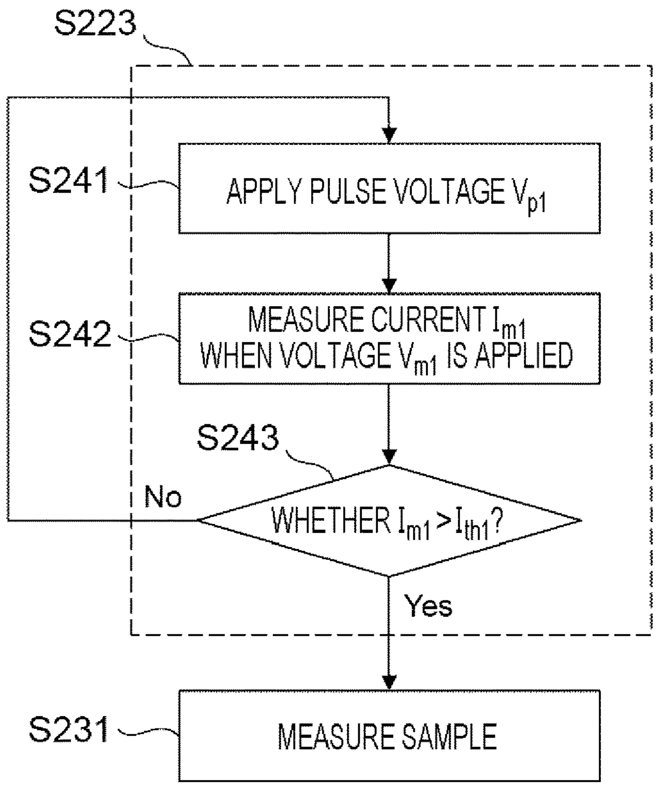
FIG. 5 is a flowchart illustrating detailed contents (example) of nanopore forming processing using a dielectric breakdown technique (pulse voltage).

(i) Example of Applying Pulse Voltage: FIG. 5

The operator uses the electric device unit 107 to apply a pulse voltage $V_{p1}$ between the Ag/AgCl electrodes 104 and 109 immersed in the first solution tank 103 and the second solution tank 110, respectively, for at least one period (step 241). Although the pulse voltage $V_{p1}$ varies in magnitude depending on thickness and material of the membrane 101, a pulse voltage of 4 V to 5 V is applied to a SiN membrane with a thickness of 5 nm, for example. The pulse voltage $V_{p1}$ serves to apply stress to the membrane 101.

Subsequently, the operator operates the electric device unit 107 to change the applied voltage from the pulse voltage $V_{p1}$ to a predetermined low voltage $V_{m1}$, and then measures a current $I_{m1}$ flowing at the low voltage $V_{m1}$ (step 242). Here, the low voltage $V_{m1}$ is set lower than a value of the pulse voltage $V_{p1}$ to such an extent that dielectric breakdown does not occur during processing in step 242 or a nanopore already formed does not expand. For example, when a SiN membrane having a thickness of 5 nm is used as the membrane 101, the low voltage $V_{m1}$ is set less than 1 V.

The operator compares the measured current $I_{m1}$ with a threshold current $I_{th1}$ (step 253). When the measured current $I_{m1}$ is larger than the threshold current $I_{th1}$ (Yes in step 243), it is determined that the nanopore 113 desired (see FIG. 2) is formed, and then the processing proceeds to step 231 (sample measuring processing). In contrast, when the measured current $I_{m1}$ is equal to or less than the threshold current $I_{th1}$ (No in step 243), the processing returns to step 241, and then the membrane 101 is stressed again by the pulse voltage $V_{p1}$. When the pulse voltage $V_{p1}$ is applied again in step 241, application time may be lengthened, or polarity (positive or negative) of the pulse voltage $V_{p1}$ to be applied may be inverted. The threshold current $I_{th1}$ to be used in step 243 can be not only estimated from the conductivity of the aqueous solution, thickness of the membrane 101, and size of the nanopore desired, but also determined (estimated) based on experiments and observation with transmission electron microscopy (TEM).

Figure 6:
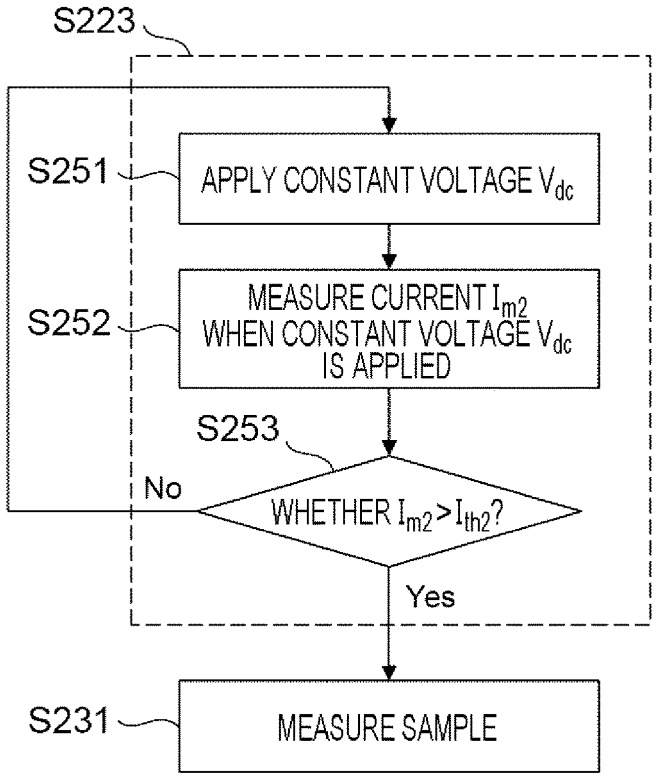
FIG. 6 is a flowchart illustrating detailed contents (example) of nanopore forming processing using a dielectric breakdown technique (constant voltage).

(ii) Example of Applying Constant Voltage: FIG. 6

The operator uses the electric device unit 107 to apply a constant voltage $V_{dc}$ between the Ag/AgCl electrodes 104 and 109 immersed in the first solution tank 103 and the second solution tank 110, respectively, for a predetermined time (step 251). Although the constant voltage $V_{dc}$ varies in magnitude depending on thickness and material of the membrane 101, a constant voltage of 16 V to 20 V can be applied to a SiN membrane with a thickness of 20 nm, for example. Application time of the constant voltage is less than 10 minutes including application time in the next step 252, for example.

Subsequently, while applying the constant voltage $V_{dc}$, the operator measures a current $I_{m2}$ flowing at that moment (step 252).

Then, the operator compares the measured current $I_{m2}$ with a threshold current $I_{th2}$, and checks whether the nanopore 113 desired is formed in the membrane 101 (step 253). When the measured current $I_{m2}$ is larger than the threshold current $I_{th2}$ (Yes in step 253), it is determined that the nanopore 113 desired (see FIG. 2) is formed, and then the processing proceeds to step 231 (sample measuring processing). In contrast, when the measured current $I_{m2}$ is equal to or less than the threshold current $I_{th2}$ (No in step 253), the processing returns to step 251, and then the constant voltage $V_{dc}$ is applied again. When the constant voltage $V_{dc}$ is applied again in step 251, a value of the constant voltage $V_{dc}$ to be applied may be increased, or polarity (positive or negative) of the constant voltage $V_{dc}$ to be applied may be inverted. The threshold current $I_{th2}$ to be used in step 253 can be not only estimated from the conductivity of the aqueous solution, thickness of the membrane 101, and size of the nanopore desired, but also determined (estimated) based on experiments and observation with transmission electron microscopy (TEM).

Figure 7:
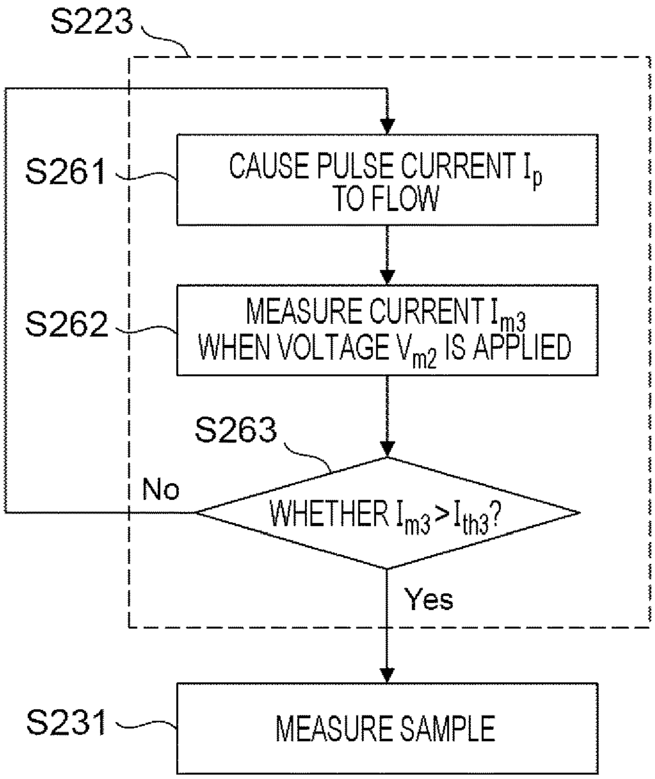
FIG. 7 is a flowchart illustrating detailed contents (example) of nanopore forming processing using a dielectric breakdown technique (pulse current).

(iii) Example of Causing Pulse Current to Flow: FIG. 7

The operator uses the electric device unit 107 to cause a pulse current $I_{p1}$ to flow between the Ag/AgCl electrodes 104 and 109 immersed in the first solution tank 103 and the second solution tank 110, respectively, for at least one period (step 261). The pulse current $I_{p1}$ varies in magnitude depending on thickness and material of the membrane 101.

Subsequently, the operator operates the electric device unit 107 to apply a predetermined low voltage $V_{m2}$ between the Ag/AgCl electrodes 104 and 109 immersed in the first solution tank 103 and the second solution tank 110, respectively, and then measures a current $I_{m3}$ flowing at the low voltage $V_{m2}$ (step 262). Here, the low voltage $V_{m2}$ is set low to such an extent that dielectric breakdown does not occur during processing in step 262 or a nanopore already formed does not expand. For example, when a SiN membrane having a thickness of 5 nm is used as the membrane 101, the low voltage $V_{m1}$ is set less than 1 V.

The operator compares the measured current $I_{m3}$ with a threshold current $I_{th3}$ (step 263). When the measured current $I_{m3}$ is larger than the threshold current $I_{th3}$ (Yes in step 263), it is determined that the nanopore 113 desired (see FIG. 2) is formed, and then the processing proceeds to step 231 (sample measuring processing). In contrast, when the measured current $I_{m3}$ is equal to or less than the threshold current $I_{th3}$ (No in step 263), the processing returns to step 261, and then the pulse current $I_{p1}$ is caused to flow between the Ag/AgCl electrodes 104 and 109 again. When the pulse current $I_{p1}$ is caused to flow again in step 261, a value of the pulse current $I_{p1}$ may be increased, or polarity (positive or negative) of the pulse current $I_{p1}$ to be caused to flow may be inverted. The threshold current $I_{th3}$ to be used in step 263 can be not only estimated from the conductivity of the aqueous solution, thickness of the membrane 101, and size of the nanopore desired, but also can be determined (estimated) based on experiments and observation with transmission electron microscopy (TEM).

Figure 8:
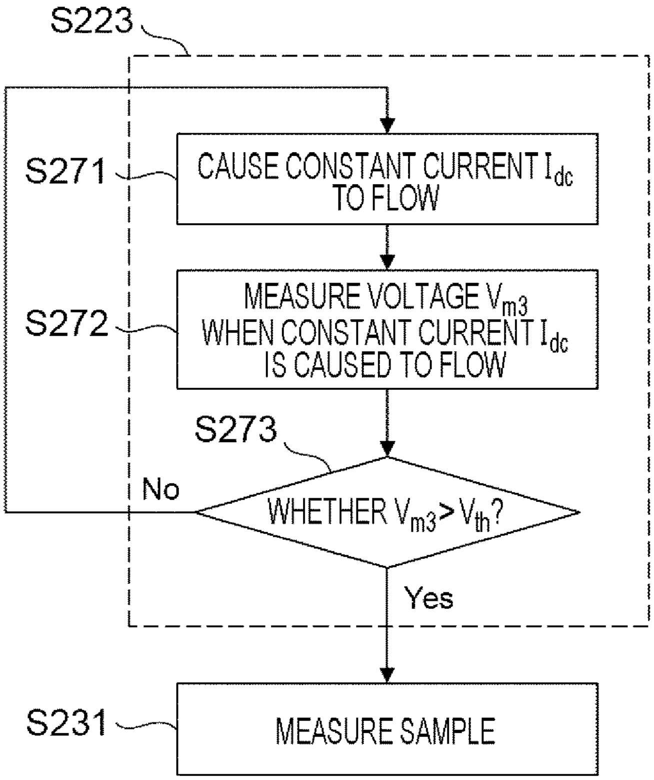
FIG. 8 is a flowchart illustrating detailed contents (example) of nanopore formation processing using a dielectric breakdown technique (constant current).

(iv) Example of Causing Constant Current to Flow: FIG. 8

The operator uses the electric device unit 107 to cause a constant current $I_{dc}$ to flow between the Ag/AgCl electrodes 104 and 109 immersed in the first solution tank 103 and the second solution tank 110, respectively, for a predetermined time (step 271). The constant current $I_{dc}$ varies in magnitude depending on thickness and material of the membrane 101. While causing the constant current $I_{dc}$ to flow, the operator measures the voltage $V_{m3}$ at that time (step 272).

Then, the operator compares the measured voltage $V_{m3}$ with a threshold voltage Vtn, and checks whether the nanopore 113 desired is formed in the membrane 101 (step 273). When the measured voltage $V_{m3}$ is larger than the threshold voltage $V_{th}$ (Yes in step 273), it is determined that the nanopore 113 desired (see FIG. 2) is formed, and then the processing proceeds to step 231 (sample measuring processing). In contrast, when the measured voltage $V_{m3}$ is equal to or lower than the threshold voltage $V_{th}$ (No in step 273), the processing returns to step 271, and then the constant current $I_{dc}$ is caused to flow again between the electrodes 104 and 109. When the constant current $I_{dc}$ is caused to flow again in step 271, a value of the constant current $I_{dc}$ may be increased, or polarity (positive or negative) of the constant current $I_{dc}$ to be caused to flow may be inverted. The threshold voltage Vtn to be used in step 273 can be not only estimated from the conductivity of the aqueous solution, thickness of the membrane 101, and size of the nanopore desired, but also can be determined (estimated) based on experiments and observation with transmission electron microscopy (TEM).

<Experimental Results>

Figure 9A:
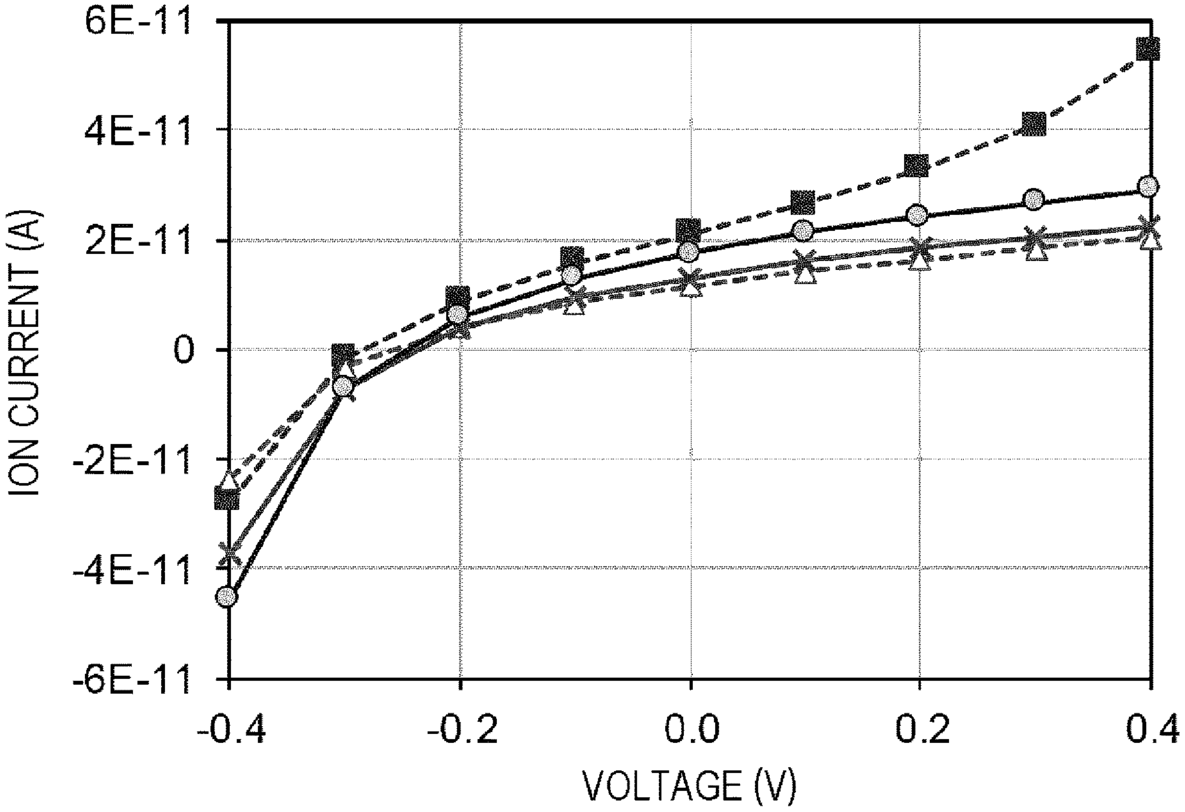
FIG. 9A is a diagram illustrating IV (current-voltage) characteristics before a nanopore is formed in a membrane 101 by a dielectric breakdown technique.
Figure 9B:
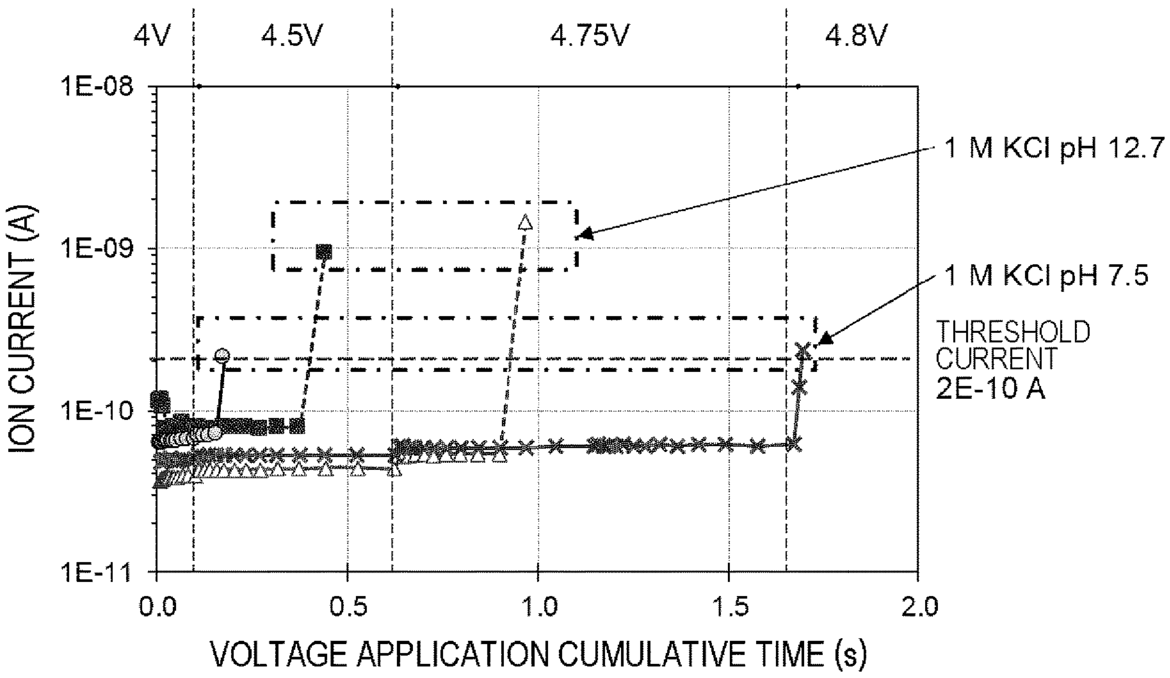
FIG. 9B is a diagram corresponding to a mode (FIG. 5) in which a pulse voltage is applied, and illustrating characteristics of a current $I_m$ (ion current) measured by increasing pulse voltage $V_p$ stepwise from 4 V to 4.8 V, and increasing a pulse period (application period of the pulse voltage) for each voltage to 200 ms, and then by applying a specific low voltage $V_m$ (e.g., 0.4 V).

FIGS. 9A and 9B are each a diagram illustrating results of experiments using the technique of the present disclosure. The experimental results include results (i) of two membranes indicated by dotted lines, the results being acquired by performing the hydrophilicity processing (S201) and the nanopore forming processing by the dielectric breakdown technique (S221) using a common high pH aqueous solution (aqueous solution at the first pH, such as 1M KCl pH 12.7, and results (ii) of two other membranes indicated by solid lines, the results being acquired by performing the hydrophilicity processing (S201) using a high pH aqueous solution (aqueous solution at the first pH, such as 1M KCl pH 12.7), and the nanopore forming processing by the dielectric breakdown technique (S221) using a neutral pH aqueous solution (aqueous solution at the second pH, such as 1M KCl pH 7.5).

FIG. 9A is a diagram illustrating IV (current-voltage) characteristics before a nanopore is formed in the membrane 101 by the dielectric breakdown technique. As illustrated in FIG. 9A, a leakage current of less than $6\times10^{-11}$ A is observed for each of the membranes. Thus, it can be seen that each of the membranes is under the same condition before the nanopore forming processing and is not broken.

FIG. 9B is a diagram corresponding to a mode (FIG. 5) in which the pulse voltage described above is applied, and illustrating characteristics of a current $I_m$ (ion current) measured by increasing pulse voltage $V_p$ stepwise from 4 V to 4.8 V, and increasing a pulse period (application period of the pulse voltage) for each voltage to 200 ms, and then by applying a specific low voltage $V_m$ (e.g., 0.4 V). In FIG. 9B, dotted line graphs (with a plot in the shape of a square and a plot in the shape of a trainable) show results of nanopore formation of the two membranes when the dielectric breakdown is caused in the aqueous solution (e.g., 1M KCl pH 12.7) at the first pH. In contrast, solid line graphs (with a plot in the shape of a circle and a plot in the shape of a cross) show results of nanopore formation of the two membranes when the dielectric breakdown is caused in the aqueous solution (e.g., 1M KCl pH 7.5) at the second pH. It can be seen from FIG. 9B that the current $I_m$ measured when a nanopore is formed in the first pH aqueous solution (1M KCl pH 12.7) greatly exceeds the threshold current $I_{th}$ while the current $I_m$ measured when a nanopore is formed in the second pH aqueous solution (1M KCl pH 7.5) stays at a value slightly above the threshold current $I_{th}$. That is, according to the former (when both the hydrophilicity processing and the nanopore forming processing are performed in the first pH aqueous solution), a nanopore was formed, however, had a size larger than a desired size. In contrast, according to the latter (the present embodiment in which the hydrophilicity processing is performed in the first pH aqueous solution, and the nanopore forming processing is performed in the second pH aqueous solution (second pH<first pH)), the desired size of a nanopore can be accurately controlled.

<Example of Measurement Result of RMS Noise in Hydrophilicity Checking Processing>

Figure 10A:
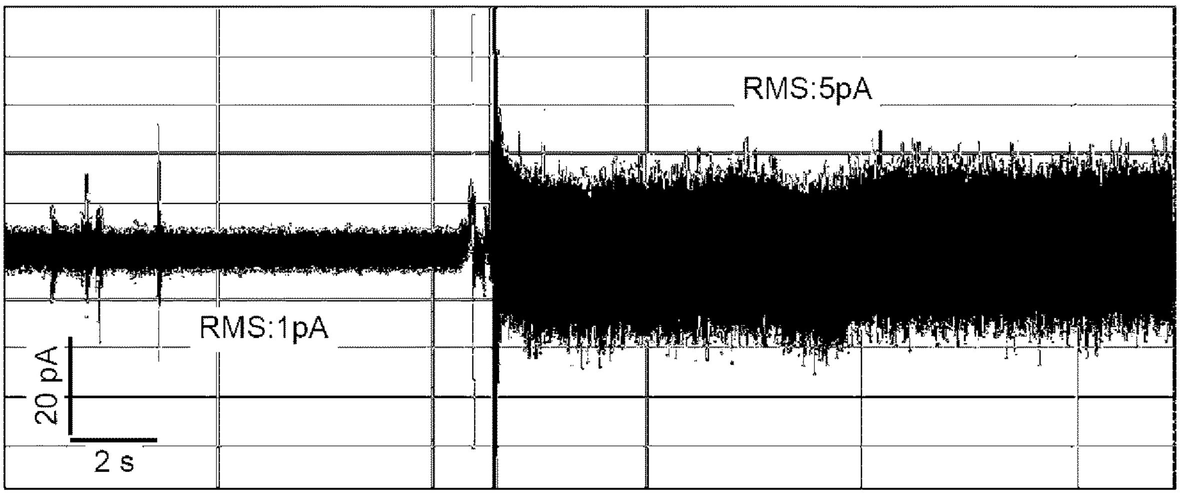
FIG. 10A is a diagram illustrating current values (current values before and after inserting electrodes 104 and 109 into a flow cell) measured when an applied direct-current (DC) voltage $V_c$ is 0 V.
Figure 10B:
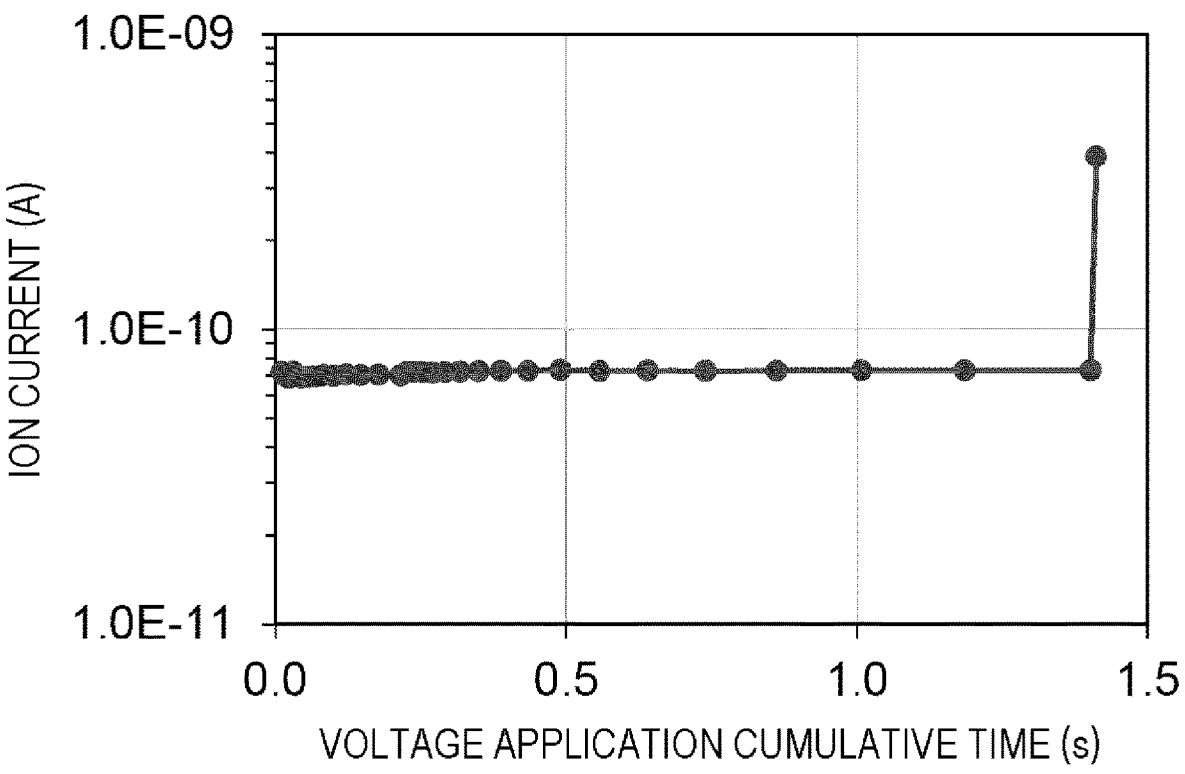
FIG. 10B is a diagram illustrating an experimental result (voltage application cumulative time–ion current characteristics) when nanopore forming processing (S221) is performed on the membrane 101 with RMS noise with a load that is several times (five times in FIG. 10A) larger than RMS noise without a load.

FIGS. 10A and 10B are each a diagram illustrating an example (experimental result) of measurement results of RMS noise in the hydrophilicity checking processing (S211). FIG. 10A is a diagram illustrating current values (current values before and after inserting electrodes 104 and 109 into a flow cell) measured when the applied DC voltage $V_c$ is 0 V. That is, FIG. 10A illustrates current values with RMS noise (RMS noise without a load) measured in step 212 to step 213 in FIG. 4 before insertion of the electrodes 104 and 109 into the flow cell, and current values with RMS noise (RMS noise with a load) measured in step 214 after the insertion of the electrodes 104 and 109 into the flow cell. FIG. 10A illustrates 1 pA that is measured as the RMS noise $\sigma_{no}$ without a load, and 5 pA that is measured as the RMS noise $\sigma_w$ with a load, for example. In this case, the RMS noise $\sigma_w$ with a load is five times the RMS noise $\sigma_{no}$ without a load. Thus, it is considered that hydrophilicity of the surface of the membrane 101 is checked, and then the subsequent nanopore forming processing is performed.

FIG. 10B is a diagram illustrating an experimental result (voltage application cumulative time–ion current characteristics) when nanopore forming processing (S221) is performed on the membrane 101 with RMS noise with a load that is several times (five times in FIG. 10A) larger than RMS noise without a load. It can be seen from FIG. 10B that the nanopore 113 is formed in the membrane 101 because a large change is observed in ion current values when the voltage application cumulative time exceeds a predetermined period (about 1.4 s in FIG. 10B). The nanopore 113 formed in the membrane 101 indicates that the surface of the membrane 101 has been successfully made hydrophilic or the aqueous solution has come into normal contact with the surface of the membrane 101. That is, it can be seen that comparing the RMS noise (FIG. 10A) is synonymous with checking a hydrophilic property of the surface of the membrane 101.

REFERENCE SIGNS LIST

101 dry membrane (SiN)
102, 111 gasket
103 first solution tank
104 electrode (Ag/AgCl)
105 electric conducting wire
106, 112 high pH aqueous solution (first pH aqueous solution)
107 electric device unit
108 electric conducting wire
109 electrode (Ag/AgCl)
110 second solution tank
113 nanopore
120 sample
130, 131 neutral pH aqueous solution (second pH aqueous solution)
140, 141 aqueous solution

The invention claimed is:

1. A nanopore formation method for forming a nanopore in a membrane, the method comprising:

introducing an aqueous solution at a first pH into a first solution tank and a second solution tank insulated by the membrane;

securing hydrophilicity of a surface of the membrane;

replacing the aqueous solution at the first pH in the first solution tank and the second solution tank with an aqueous solution at a second pH lower than the first pH after the hydrophilicity of the surface of the membrane is secured; and immersing an electrode in each of the first solution tank and the second solution tank containing the aqueous solution at the second pH to cause dielectric breakdown and form the nanopore in the membrane, wherein securing the hydrophilicity of the surface of the membrane includes:

applying a voltage to the electrodes without immersing the electrodes in the first solution tank and the second solution tank containing the aqueous solution at the first pH to measure a first capacitance noise;

applying a voltage to the electrodes by immersing the electrodes in each of the first solution tank and the second solution tank that contain the aqueous solution at the first pH to measure a second capacitance noise; and checking the hydrophilicity of the surface of the membrane by comparing the first capacitance noise with the second capacitance noise.

2. The nanopore formation method according to claim 1, wherein the first capacitance noise is measured by measuring root mean square noise at a direct-current voltage of less than 10 V.

3. The nanopore formation method according to claim 2, wherein securing the hydrophilicity of the surface of the membrane is determined when the second capacitance noise is higher than the first capacitance noise by twice or more.

4. The nanopore formation method according to claim 1, wherein the membrane includes a silicon nitride layer.

5. The nanopore formation method according to claim 4, wherein the silicon nitride layer has a thickness of less than 100 nm.

6. The nanopore formation method according to claim 1, wherein the first pH is 8 or more.

7. The nanopore formation method according to claim 1, wherein the first pH is 10 or more.

8. The nanopore formation method according to claim 1, wherein forming the nanopore in the membrane includes:

applying a constant voltage to the electrodes;

measuring a current flowing while the constant voltage is applied; and determining that the dielectric breakdown is caused when the current is larger than a threshold current.

9. The nanopore formation method according to claim 1, wherein forming the nanopore in the membrane includes:

causing a pulse current to flow to the electrodes;

measuring a current flowing while a predetermined voltage is applied to the electrodes; and determining that the dielectric breakdown is caused when the current is larger than a threshold current.

10. The nanopore formation method according to claim 1, wherein forming the nanopore in the membrane includes:

causing a constant current to flow to the electrodes;

measuring a potential of the electrodes while the constant current is caused to flow; and determining that the dielectric breakdown is caused when the potential is smaller than a threshold potential.

11. A nanopore formation method for forming a nanopore in a membrane, the method comprising:

introducing an aqueous solution at a first pH into a first solution tank and a second solution tank insulated by the membrane;

securing hydrophilicity of a surface of the membrane;

replacing the aqueous solution at the first pH in the first solution tank and the second solution tank with an aqueous solution at a second pH lower than the first pH after the hydrophilicity of the surface of the membrane is secured; and immersing an electrode in each of the first solution tank and the second solution tank containing the aqueous solution at the second pH to cause dielectric breakdown and form the nanopore in the membrane, wherein securing the hydrophilicity of the surface of the membrane is determined when a second capacitance noise is higher than a first capacitance noise by twice or more, and wherein forming the nanopore in the membrane includes:

applying a pulse voltage to the electrodes;

measuring a current flowing when a voltage lower than the pulse voltage is applied to the electrodes; and determining that the dielectric breakdown is caused when the current is larger than a threshold current.

12. The nanopore formation method according to claim 11, wherein the membrane includes a silicon nitride layer.

13. The nanopore formation method according to claim 11, wherein the silicon nitride layer has a thickness of less than 100 nm.

14. The nanopore formation method according to claim 11, wherein the first pH is 8 or more.

15. The nanopore formation method according to claim 11, wherein the first pH is 10 or more.

16. A nanopore formation method for forming a nanopore in a membrane, the method comprising:

introducing an aqueous solution at a first pH into a first solution tank and a second solution tank insulated by the membrane;

preparing an electric device that applies a voltage between electrodes or causes a current to flow between the electrodes;

applying a direct-current voltage of less than 10 V between the electrodes using the electric device in a state without a load to measure a first square root noise;

applying the direct-current voltage of less than 10 V between the electrodes using the electric device in a state with a load to measure a second square root noise;

replacing the aqueous solution at the first pH in the first solution tank and the second solution tank with an aqueous solution at a second pH lower than the first pH after hydrophilicity of a surface of the membrane is secured; and immersing an electrode in each of the first solution tank and the second solution tank containing the aqueous solution at the second pH to cause dielectric breakdown and form the nanopore in the membrane.

17. The nanopore formation method according to claim 16, wherein the state without a load is defined as a state in which the electrodes are not immersed in the first solution tank and the second solution tank that contain the aqueous solution at the first pH, and the state with a load is defined as a state in which the electrodes are immersed in the first solution tank and the second solution tank that contain the aqueous solution at the first pH.

* * * * *